US007029561B2

(12) United States Patent
Ross et al.

(10) Patent No.: US 7,029,561 B2
(45) Date of Patent: Apr. 18, 2006

(54) FLUIDIC TEMPERATURE GRADIENT FOCUSING

(75) Inventors: David Ross, Silver Spring, MD (US); Laurie E. Locascio, North Potomac, MD (US)

(73) Assignee: The United States of America as represented by the Secretary of Commerce, Washington, DC (US)

( * ) Notice: Subject to any disclaimer, the term of this patent is extended or adjusted under 35 U.S.C. 154(b) by 483 days.

(21) Appl. No.: 10/197,331

(22) Filed: Jul. 18, 2002

(65) Prior Publication Data

US 2003/0019752 A1 Jan. 30, 2003

Related U.S. Application Data

(60) Provisional application No. 60/323,404, filed on Sep. 19, 2001, provisional application No. 60/307,691, filed on Jul. 25, 2001.

(51) Int. Cl.
*G01N 27/447* (2006.01)
*G01N 27/453* (2006.01)

(52) U.S. Cl. .................. 204/451; 204/601; 204/450; 204/600

(58) Field of Classification Search ........ 204/451–455, 204/601–605, 450, 600
See application file for complete search history.

(56) References Cited

U.S. PATENT DOCUMENTS

| 3,664,939 A | | 5/1972 | Luner et al. |
| 5,021,646 A | * | 6/1991 | Weinberger et al. ... 250/227.11 |
| 5,759,370 A | | 6/1998 | Pawliszyn |
| 5,795,720 A | * | 8/1998 | Henco et al. ............ 435/6 |
| 6,277,258 B1 | * | 8/2001 | Ivory et al. ............ 204/450 |
| 6,749,735 B1 | * | 6/2004 | Le Febre .............. 204/601 |

OTHER PUBLICATIONS

Grushka et al. (Effect of Temperature Gradients on the Efficiency of Capillary Zone Electrophoresis Separations, Anal. Chem. 1989, 61, 241-246), Feb.*
Hinckley ("Electrophoretic Thermal Theory: I Temperature Gradients and their Effects," Journal of Chromatography, 109 (1975 209-217), Jun.*
Knox et al. (Temperature Effects in Capillary Electrophoresis. 1: Internal Capillary Temperature and Effect upon Performance. Chromatographia vol. 38, No. 3/4 Feb. 1994).*
Birmes et al. ("Analysis of the conformational transitions of proteins by temperature-gradient gel electrophoresis," Electrophoresis 1990, 11, 795-801), month unknown.*

(Continued)

*Primary Examiner*—Alex Noguerola
(74) *Attorney, Agent, or Firm*—Stites & Harbison PLLC; Ross F. Hunt, Jr.

(57) ABSTRACT

A method and device are provided for concentrating and separating ionic species in solution within a fluidic device having a fluid conduit such as a channel or capillary. The concentration is achieved by balancing the electrophoretic velocity of an analyte against the bulk flow of solution in the presence of a temperature gradient. Using an appropriate buffer, the temperature gradient can generate a corresponding gradient in the electrophoretic velocity so that the electrophoretic and bulk velocities sum to zero at a unique point and the analyte will be focused at that point. The method and device may be adapted for use with a variety of analytes including fluorescent dyes, amino acids, proteins, DNA and to concentrate a dilute analyte.

37 Claims, 6 Drawing Sheets

OTHER PUBLICATIONS

Liu et al. ("Separation of Chlorophenols by Capillary Zone Electrophoresis. The influence of pH of the Electrophoretic Buffer on Selectivity," Short Communications J. High Resol. Chromatogr., vol. 21, May 1998).*

Grossman et al. ("Effect of Buffer pH and Peptide Composition on the Selectivity of Peptide Separations by Capillary Zone Electrophoresis," Analytical Biochemistry 173, 265-270 (1988)), Sep.*

Lochmüller et al.; "Open-Channel Isoelectric Focusing In Thermally Engendered pH Gradients"; *Journal of Chromatography*, 480 (1989); pp. 293-399.

Liang Zhu, Hian Kee Lee, Bingcheng Lin and Edward S. Yeung, "Spatial temperature gradient capillary electrophoresis for DNA mutation detection", *Electrophoresis*, 22, 3683-3687 (2001).

Roger M. Wartell, Seyed Hosseini, Sandra Powell and Jian Zhu, "Detecting single base substitutions, mismatches and bulges in DNA by temperature gradient gel electrophoresis and related methods", *Journal of Chromatography A*, 806, 169-185 (1998).

Chen-Wen Whang and Edward S. Yeung, "Temperature Programming in Capillary Zone Electrophoresis", *Anal. Chem.*, 64, 502-506 (1992).

B. Crane, C. Hogan, L. Lerman and I.W. Hunter, "DNA mutation detection via fluorescence imaging in a spatial thermal gradient, capillary electrophoresis system", *Review of Scientific Instruments*, vol. 72, 11, 4245-4251 (2001).

* cited by examiner

PRIOR ART

PRIOR ART

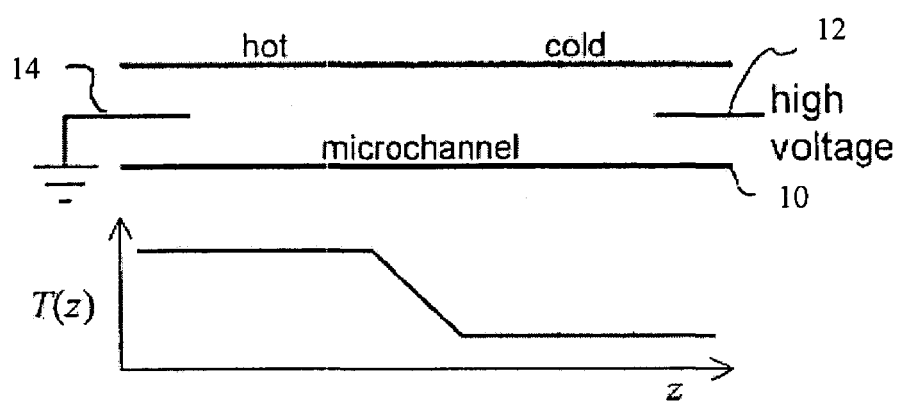
Fig. 3(a)
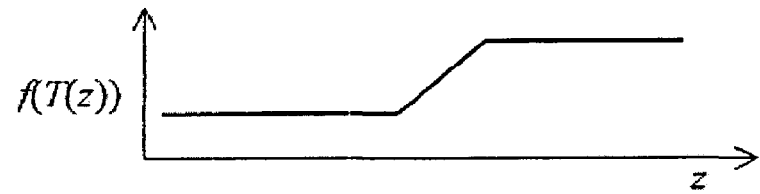
Fig. 3(b)
Fig. 3 (c)
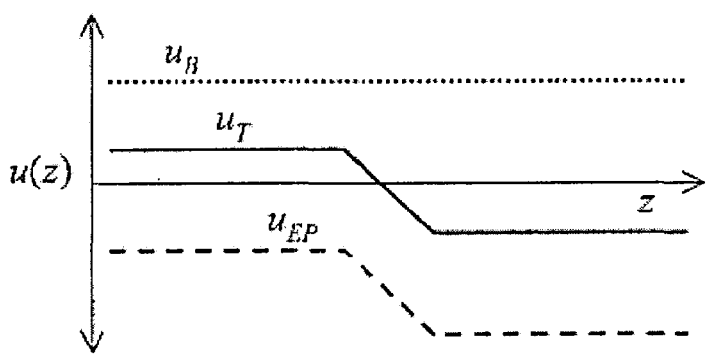
Fig. 3 (d)

FLUIDIC TEMPERATURE GRADIENT FOCUSING

CROSS-REFERENCE TO RELATED APPLICATIONS

This application claims benefit of the filing date of both copending Provisional Patent Application Nos. 60/307,691, filed on Jul. 25, 2001, and 60/323,404, filed on Sep. 19, 2001.

STATEMENT REGARDING FEDERALLY SPONSORED RESEARCH

This invention was made by employees of the United States Government and may be manufactured and used by or for the Government for governmental purposes without the payment of any royalties.

FIELD OF THE INVENTION

The present invention relates to a method for electrokinetic focusing of samples, and in particular, methods for electro-focusing samples in fluidic devices using electric field gradients.

BACKGROUND OF THE INVENTION

Over the past decade a great deal of research has been focused on the development of technology related to micro-total-analytical systems. This technology is based on the concept of a series of microfluidic channels also known as microchannels for the movement, separation, reaction, and/or detection of various chemicals or biological compounds such as amino acids, proteins, and DNA.

One disadvantage with prior microfluidic devices is that there is frequently a mismatch between the extremely small quantities of sample used for analysis and the often much larger quantities needed for loading the sample into the microfluidic device and transporting the sample to the point of analysis. For example, a typical analysis sample may be around one nanoliter or less of a liquid containing sample that is injected into a separation channel and then separated electrokinetically as it moves down the channel to a detection region. However, the channels used to transport the sample to the injection point are typically also filled with the sample, thus increasing the required amount of the sample by a factor of 100 or more. In addition, the sample is typically loaded onto the microfluidic device into a reservoir from a pipette so that in all, approximately 99.9% of the sample is discarded as waste.

Electric field gradient focusing is one way of addressing the problem of requiring a large sample for analysis due to the inefficiencies of conventional devices which result in wasted sample. Electric field gradient focusing can be used to concentrate samples at a given point within a microfluidic device before the analysis step. Further, the electric field gradient can be used to concentrate all of the sample at the beginning of the separation channel so that very little of the sample would be wasted.

Electric field gradient focusing is accomplished by the application of an electric field gradient within a microchannel. In response to the electric field gradient, there is a corresponding gradient in the electrophoretic velocity of any ion within the microchannel. The total velocity of the ion is the sum of its electrophoretic velocity and the bulk fluid velocity. If these two components of the velocity are in opposite directions, they can be balanced so that the molecule will have zero total velocity.

When there is a gradient in the electrophoretic velocity, the balance between bulk and electrokinetic velocities can occur at a single point within the microchannel and therefore can result in focusing of ions at that point. Typically, the electric field gradient used in focusing is generated by the external manipulation of the electric field in the middle of the microchannel through the use of conducting wires, salt bridges, porous membranes, or other structures that will pass electric current but will restrict the flow of bulk fluid and analytes that are to be focused.

Several recent developments with regard to focusing methods in microfluidics, and in particular, the use of electric field gradients, have been made. A description of related methods of focusing can be found in C. F. Ivory, W. S. Koegler, R. L. Greenlee, and V. Surdigio, Abstracts of Papers of the American Chemical Society 207, 177-BTEC (1994); C. F. Ivory, Separation Science and Technology 35, 1777 (2000); Z. Huang and C. F. Ivory, Analytical Chemistry 71, 1628 (1999); W. S. Koegler and C. F. Ivory, Journal of Chromatography a 726, 229 (1996); and P. H. Ofarrell, Science 227, 1586 (1985), all of which are hereby incorporated by reference.

To illustrate the basic principles disclosed in these publications, reference is made to FIG. 1(a) which depicts a length of buffer-filled microchannel of constant cross-sectional area with an electrode, denoted 4, in the middle, and two further electrodes at each end, denoted 3 and 5, so that the voltages $V_1$, $V_3$ at the ends and the voltage $V_2$ at the middle of the channel can be controlled. A single species of negatively charged analyte is present in a buffer that is provided to the microchannel. The electrical connection, represented as electrode 4, can be accomplished with a simple metal wire as depicted in FIG. 1(a), or through a more complicated structure consisting of additional fluid channels and porous membrane structures or salt bridges.

The electric field in the section 1, i.e., the channel between electrodes 3 and 4 is $E_1=(V_2-V_1)/(l/2)$ and the electric field in section 2, i.e., between electrodes 4 and 5, is $E_2=(V_3-V_2)/(l/2)$, where $V_1$, $V_2$, and $V_3$ are the voltages applied to the three electrodes 3, 4, and 5, and l is the length of the microchannel. If, $E_1$ differs from $E_2$ as shown in FIG. 1(b), the electrophoretic velocity of the analyte in the channel, $u_{EP}$, will be different in section 1 than in section 2. If an overall bulk fluid velocity, $u_B<0$, is applied, e.g., either electro-osmotic or pressure-driven, the bulk fluid velocity must be the same, due to continuity, in all parts of the microchannel. The total velocity of the analyte, $u_T=u_B+u_{EP}$, will then be the sum of the electrophoretic and bulk velocities, which can differ in section 1 from section 2.

The use of the microchannel device of FIG. 1(a) for focusing of the ions is illustrated in FIG. 2 where $u_{T,1}>0>u_{T,2}$, so that the ions flow into the middle from both directions and are thus focused in the middle of the channel near electrode 4.

One major drawback to electric field gradient focusing is that the microchannel device tends to be difficult to construct and that it requires the control of voltage on an additional electrode, e.g. 4 of FIG. 1(a), that is used to apply the electric field gradient. In addition, if electrodes are used to generate electric field gradients, unwanted chemical products will be generated electrochemically at the buffer-electrode interface. If the electric field gradient is produced through the use of a salt bridge or membrane, the electrochemical products can be avoided, however only chemical species that cannot pass through the membrane or salt bridge can be focused.

Two additional methods for concentrating a sample include sample stacking and field amplified sample injection in which a sample is concentrated as the sample crosses a boundary between low and high conductivity buffers. These methods can achieve preconcentration factors of 100 to 1000-fold although these methods require multiple buffers. Sweeping is yet another concentration method which is capable of a very high degree of sample concentration (e.g., up to 5000-fold), but is useful only for small hydrophoic analytes with a high affinity for a mobile micellular phase.

An additional technique for concentrating an ionic sample includes isoelectric focusing. Isoelectric focusing is commonly used for the concentration and separation of proteins and involves the focusing of analytes at their respective isoelectric points (pIs) along a pH gradient.

Two examples of recent isoelectric focusing techniques are provided by U.S. Pat. No. 3,664,939 to Luner et al. and U.S. Pat. No. 5,759,370 to Pawliszyn. Both references relate to isoelectric focusing with pH gradients that are created by the application of a temperature gradient. The isoelectric focusing uses a pH gradient to focus analytes and in particular proteins, at their isoelectric points. The isoelectric point is the pH at which the analyte has zero electrophoretic mobility, i.e., approximately zero charge. pH gradients for isoelectric focusing are typically generated using ampholyte mixtures or immobilized ampholytes in gels. The two above referenced patents are included here as examples of prior art uses of temperature gradients for focusing. It is actually very unusual for isoelectric focusing to be done with a pH gradient generated with using a temperature gradient.

One disadvantage with isoelectric focusing is that it is limited in application because it can only be used with analytes with an accessible pI. Additionally, the concentration to which a protein can be focused with isoelectric focusing is severely limited due to the low solubility of most proteins at their pIs.

BRIEF SUMMARY OF THE INVENTION

The present invention concerns a method and device for concentrating and separating ionic species in solution within fluid conduits which include channels, microchannels, and capillary tubes. The concentration is achieved by balancing the electrophoretic velocity of an analyte against the bulk flow of solution in the presence of a temperature gradient. Using an appropriate buffer, the temperature gradient can generate a corresponding gradient in the electrophoretic velocity so that the electrophoretic and bulk velocities sum to zero at a unique point and the analyte will be focused at that point. The present invention may be adapted for use with any charged analyte, including fluorescent dyes, amino acids, proteins, DNA, cells, and particles and may provide up to or, in some instances, exceed a 10000-fold concentration of a dilute analyte.

One aspect of the present invention concerns a method for directing ionic analytes contained in an ionic buffer solution of a system and which may include concentrating or separating analytes present in the buffer solution. The method includes producing an electric current flow in an ionic buffer solution containing at least one species of ionic analyte to cause the analyte ions to migrate electrophoretically. A temperature gradient is established in the buffer solution to have a significant component substantially aligned with the current flow, to thereby generating a gradient of the electrophoretic velocity of the analytes. A bulk flow is produced in the buffer solution such that the bulk flow has a significant component substantially aligned in the direction opposite the direction of the electrophoretic migration of one or more of the analytes so that the total velocity of one or more of the analytes is equal to zero at some point in the system.

According to another aspect of the present invention, a fluidic device includes a fluid conduit and an ionic buffer disposed in the conduit. At least one source or sink of heat, thermally coupled to the fluid conduit, is provided for establishing a temperature gradient having a significant component substantially aligned with the current flow so as to form an electrophoretic velocity gradient within the fluid conduit. A voltage potential source is provided for applying an electric field along a length of the fluid conduit and a current source provides an electric current flow through the ionic buffer in the fluid conduit. A source of bulk fluid flow provides for an opposing flow of the buffer in the fluid conduit. In alternate, further embodiments, the ionic buffer has either a temperature dependent ionic strength or a temperature dependent pH such that when a temperature gradient is applied to the fluid conduit, an electrophoretic velocity gradient is established in the ionic buffer present in the fluid conduit.

One advantage or feature of the present invention is provided by a technique that allows for simultaneous concentration and separation in a manner similar to isoelectric focusing but which is adoptable for use with any charged analyte and is not limited to molecules for a specific pI or range of pIs. Further, the temperature gradient focusing of the present invention can be used to achieve higher degrees of sample concentration, e.g., more than 10,000 fold concentration of a dilute sample, when compared with any prior single sample preconcentration method.

A further feature of the present invention is that the electrophoretic velocity gradient is formed within the channel or capillary in response to the temperature gradient without the need for externally manipulated voltages or complicated and difficult to fabricate semi-permeable structures.

Further features and advantages of the present invention will be set forth in, or apparent from, the detailed description of preferred embodiments thereof which follows.

BRIEF DESCRIPTION OF THE DRAWINGS

The invention will now be described in detail with respect to preferred embodiments with reference to the accompanying drawings, wherein:

FIG. 3(a) is a schematic illustration of temperature gradient focusing and fluid conduit in the form of a microchannel in accordance with the present invention, FIG. 3(b) depicts temperature distribution along the microchannel of FIG. 3(a), and FIG. 3(c) is a plot of the function $$f(T) = \frac{\sigma(20) \cdot \eta(20)}{\sigma(T) \cdot \eta(T)}$$

plotted as a function of the distance along the microchannel of FIG. 3(a), and FIG. 3(d) is a plot depicting velocity as a function of distance along the microchannel;

DETAILED DESCRIPTION OF THE INVENTION

Figure 1A:
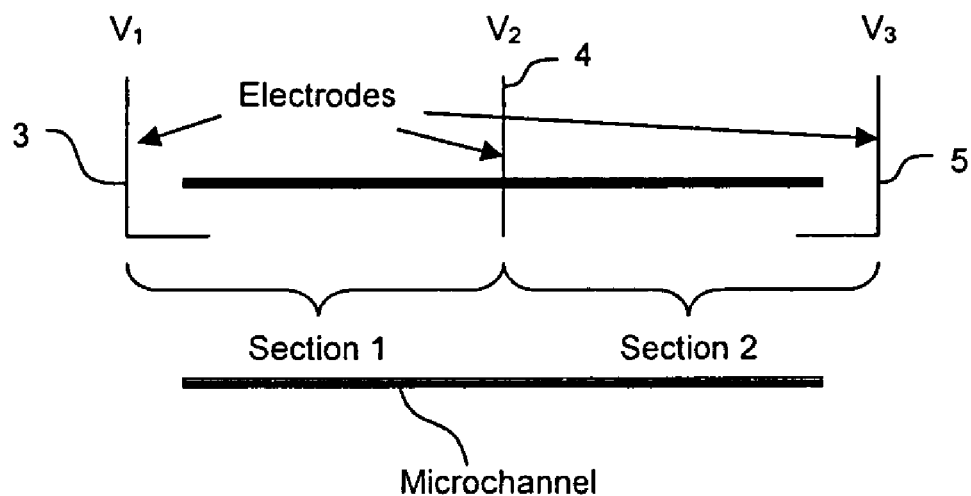
FIG. 1(a) is a schematic depicting a prior art microchannel device which provides for electric field gradient and FIG. 1(b) is a plot of the electric field versus distance (x) along the microchannel of FIG. 1(a)
Figure 1B:
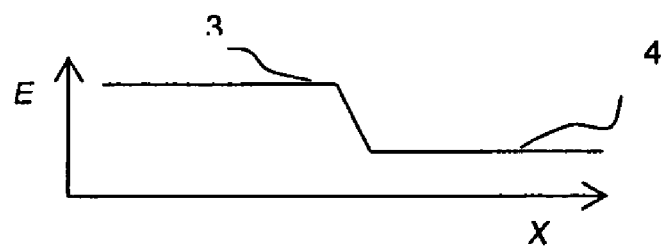
Figure 2:
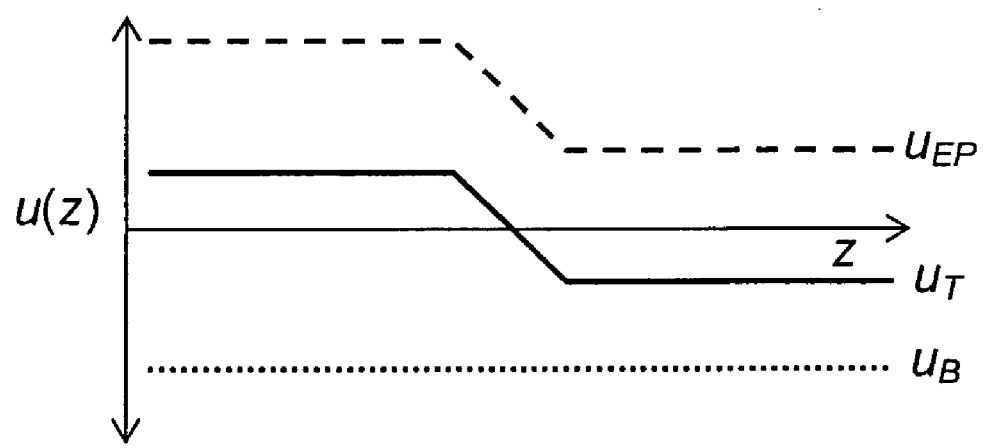
FIG. 2 is a plot of velocity versus distance along the microchannel of FIG. 1(a)

The present invention provides temperature gradient focusing of a sample in a fluidic device which includes a fluid conduit such as a channel or capillary tube. Temperature gradient focusing focuses analytes by balancing the electrophoretic velocity of an analyte against the bulk velocity of the buffer containing the analyte. If there is an appropriate gradient in the electric field, the total velocity of a given charged analyte, as determined by the sum of the bulk and electrophoretic velocities, can be set to zero at any point along the channel and all the analyte in the system is moved toward that point. However, in contrast to electric field gradient focusing where the electric field gradient is applied using a combination of electrodes and membranes, using temperature gradient focusing of the present invention, the necessary electric field gradient is produced by the application of a temperature gradient.

Further description of the present invention will now be made with reference to the drawings, and in particular to FIG. 3(a), where a buffer-filled microchannel 10 includes electrode connections 12, 14 at each end. The velocity of an analyte in the microchannel 10 is given by the sum of its electrophoretic velocity, $u_{EP}$, and the bulk velocity, $u_B$, of the buffer:

$$u_T = u_{EP} + u_B.$$

If there is a gradient in the electrophoretic velocity, the bulk velocity can be adjusted so that the total velocity is equal to zero at a single point along the channel, and the analyte will be focused at that point. The electrophoretic velocity of an analyte in the microchannel 10 is given by the product of the electric field, E, and the electrophoretic mobility of the analyte: $u_{EP} = E \cdot \mu_{EP}$.

A temperature gradient is applied along the length of the channel as shown in FIG. 3(b). This results in corresponding gradients in both the electric field E and the electrophoretic mobility $\mu_{EP}$.

The electric field in the microchannel 10 is given by:

$$E = \frac{I}{A \cdot \sigma},$$

where I is the electric current running through the microchannel 10, A is the channel cross-sectional area of the microchannel 10, and σ is the conductivity of the buffer.

Since the conductivity of the buffer is temperature-dependent, the electric field is also temperature-dependent. Here, constant current is presumed because the current running through any given section of the microchannel 10 will be the same for all parts of the microchannel, whereas the voltage drop across a portion of the microchannel 10 and the electric field in the microchannel 10 will depend on the temperature of that portion. One skilled in the art will readily appreciate that the present temperature gradient focusing differs from electric field gradient focusing in that in electric field gradient focusing, the velocity gradient that is used for focusing results from a gradient in the electric field imposed by the addition or subtraction or current from point or points within the microchannel.

Using microchannel 10, it is possible to manipulate the conductivity of the buffer by changing the temperature. Consequently, it is possible to produce electric field gradients in microfluidic devices, such as microchannel 10, through the application of a temperature gradient.

At fixed current density, the electric field in microchannel 10 is inversely proportional to the conductivity of the buffer solution in the microchannel. Most often, the primary temperature dependence of the conductivity is due to the variation of the solvent viscosity with temperature, so it can be written as $\sigma = \sigma_0 \cdot \eta(20)/(\eta(T) \cdot f(T))$, where σ is the conductivity, $\sigma_0$ is a constant, $\eta(T)$ is the temperature dependent viscosity, and $f(T)$ is a function that accounts for any other temperature dependence. Similarly, the temperature dependence of the electric field is given by $E = E_0 \cdot \eta(T) \cdot f(T)/\eta(20)$, where E is the electric field and $E_0$ is a constant.

For most buffers, the function $f(T)$ is constant or only weakly dependent on temperature. However, it can be non-constant, i.e., variable, if, for example, the ionic strength of the buffer is temperature dependent. Advantageously, the buffers of the present invention are characterized by a non-constant $f(T)$.

The electrophoretic mobility of an ionic (e.g., analyte) species in the buffer is also dependent on the viscosity, and so can be written as $\mu_{EP} = \mu_0 \cdot \eta(20)/(\eta(T) \cdot f_{EP}(T))$, where $\mu_0$ and $f_{EP}(T)$ are defined in analogy to $\sigma_0$ and $f(T)$ where, for most analytes, $f_{EP}(T)$ will be constant. The electrophoretic velocity of the analyte can then be written as $u_{EP} = E_0 \cdot \mu_0 \cdot f(T)/f_{EP}(T)$. It should be noted that if $f(T)$ and $f_{EP}(T)$ have the same temperature dependence, e.g., they are both constant, then $u_{EP}$ will not be temperature dependent, and an electric field gradient produced in this way can not be used for focusing.

If, on the other hand, $f(T)$ and $f_{EP}(T)$ do not have the same temperature dependence, then temperature gradients will result in gradients in the electrophoretic velocity, which can be used for focusing as described above.

One skilled in the art will readily appreciate a major advantage of this present method over some other methods of preconcentration is that the concentration of the buffer salts is completely unaffected by the focusing. This results from the fact that if the buffer salt is considered as an analyte, then, by definition, $f_{EP}(T) = f(T)$ and there is no gradient in the electrophoretic velocities of the buffer salts.

Most commonly this technique would be implemented with a buffer characterized by a strongly temperature dependent $f(T)$ and with analytes characterized by a constant or nearly constant $f_{EP}(T)$. However, the present temperature gradient focusing can also be implemented in a system in which $f(T)$ is constant and $f_{EP}(T)$ is not, or in which both $f(T)$ and $f_{EP}(T)$ are non-constant, but differ in their temperature dependence.

The counterbalancing bulk flow can be applied electroosmotically if the electro-osmotic mobility does not differ too much from the electrophoretic mobility of the analyte. If the electro-osmotic mobility is written as $\mu_{EO}=\mu_{EO}^0 \cdot \eta(20)/\eta(T)$, then by adjusting the ratio of the lengths of the hot and cold channels, (assuming $f_{EP}(T)=$constant) focusing can be achieved if $f(\text{cold})/f(\text{hot})<-\mu_0/\mu_{EO}^0<f(\text{hot})/f(\text{cold})$, where $f(\text{hot})>f(\text{cold})$. If $f(\text{hot})<f(\text{cold})$, then the inequalities have the opposite sign. If x is the fraction of the total channel length that is hot, then focusing will occur if: $x \cdot f(\text{hot})/f(\text{cold})+(1-x)<-\mu_0/\mu_{EO}^0<x+(1-x)\cdot f(\text{cold})/f(\text{hot})$, where $f(\text{hot})>f(\text{cold})$. By adjusting x, it is then possible to tune the range of analyte mobilities that are focused.

It should be noted that this can also be done for microchannels of non-constant cross-section. The final results are essentially unchanged, since in most instances, the dependence on the cross-sectional area of the channel cancels out in the equations. As a result, it is possible to generate the temperature gradient using Joule heating within the microchannel. This would serve to simplify the design and operation of a microfluidic device using this technique even further, since the focusing and the temperature gradient could be produced using the same pair of electrodes as illustrated in FIG. 4(a).

Figure 4A:
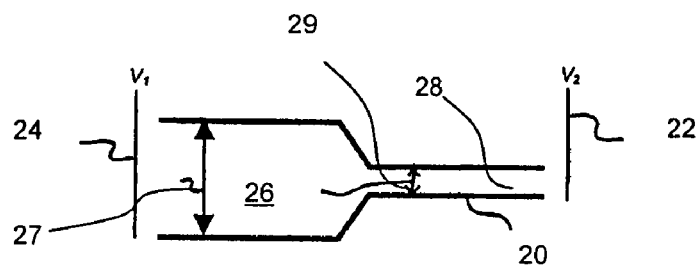
FIG. 4(a) is a schematic illustration of a microchannel for temperature gradient focusing created by Joule heating according to another embodiment of the present invention.
Figure 4B:
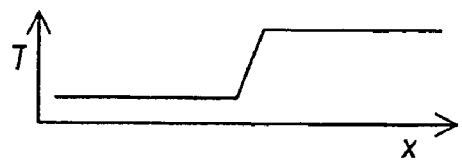
FIG. 4(b) depicts the temperature profile along a length of the microchannel of FIG. 4(a)
Figure 4:
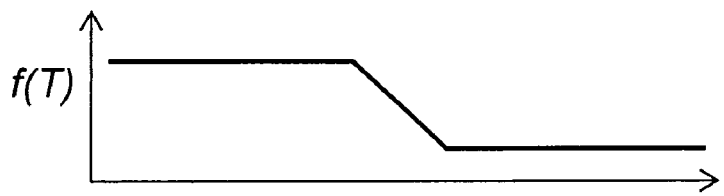
FIG. 4(c) depicts the electric field profile along a length of the microchannel of FIG. 4(a)
FIG. 4(d) is a plot showing electrophoretic velocity, bulk velocity, and total velocity vs. distance along the microchannel of FIG. 4(a)
Figure 4:
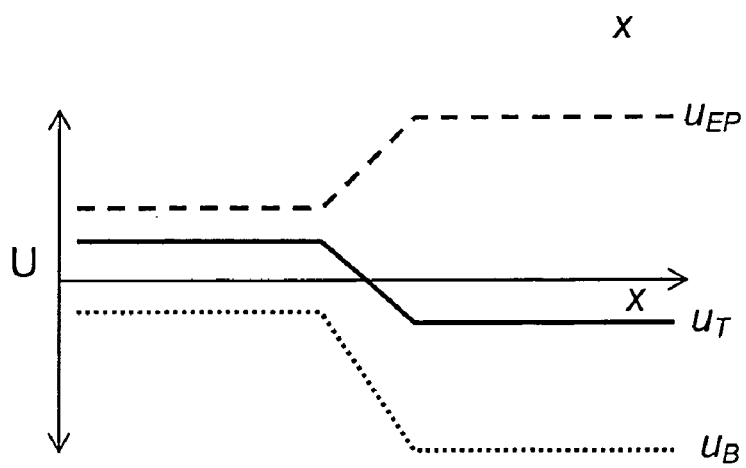

Microchannel 20 shown schematically in FIG. 4(a), has electrodes, 22, 24, and two sections, sections 26, 28, of different cross-sectional area. Section 26 has a cross-sectional area of 27 and section 28 has a cross-sectional area of 29. The electrical resistance per unit length of each section is given by: $R_1=1/(\sigma \cdot A_1)$, where $\sigma$ is the conductivity of the buffer in the microchannel 20. When a current, I, is passed through the microchannel 20, the power per unit length dissipated through Joule heating in each section will be: $P_1=I^2 \cdot R_1=I^2/(\sigma \cdot A_1)$. In general, the resulting temperature in section 28 will be higher than that in section 26, as shown in FIG. 4(b): $T_2>T_1$. The electric field in each section of the microchannel 20 is given by the current multiplied by the resistance per unit length: $E_i=I \cdot R_i=I/(\sigma A_i)=I \cdot \eta(T_i) \cdot f(T_1)/(\sigma_0 \cdot h(20) \cdot A_i)$.

The electrophoretic velocity of an analyte in each section of the channel is: $u_{EP}^i=\mu_0 \cdot f(T)_1) \cdot I/(\sigma_0 \cdot f_{EP}(T) \cdot A_1)$. If a bulk flow velocity is applied along the channel, it will not be the same in each section, but will instead be given by $u_B^i=u_B^0/A_i$, where, $u_B^0$ is a constant. The ratio of the electrophoretic velocity to the bulk velocity is then given by: $u_i^{ratio}=\mu_0 \cdot f(T_i) \cdot I/(\sigma_0 \cdot f_{EP}(T) \cdot u_B^0) \equiv u_0^{ratio} \cdot f(T_i)/f_{EP}(T)$ via adjusting $u_B^0$ so that $|u_1^{ratio}|>1>|u_2^{ratio}|$ as shown in FIG. 4(d), which can result in focusing. Because the ratio of the electrophoretic velocity to the bulk velocity does not depend on the cross-sectional areas of the two sections, the same considerations as above apply if bulk flow is applied electroosmotically.

One preferred buffer system is composed of 0.9 mol/L Trizma base and 0.9 mol/L boric acid in water (1.8 M Tris/boric), with an expected pH of about 8.7 (at room temperature). From measurements of the conductivity of the buffer, the function $f(T)$ was determined to vary from 1 at 20° C. to 0.77 at 70° C.

Joule heating may be used to generate the temperature gradient in the microchannel device of FIG. 4(a). The following is a non-limiting example demonstrating Joule heating of a microchannel of the type shown in FIG. 4(a).

The microchannel used for this demonstration was similar to the one shown schematically in FIG. 4(a). The width, i.e., cross sectional area 29, of the narrow channel, i.e., section 28, was about 70 μm, and the width of the wide section, i.e., section 26, was of the cross sectional area 26 was about 350 μm. The length of the tapered portion of the channel was about 500 μm. The depth of all portions of the channel was about 30 μm. The total length of the microchannel was about 2 cm, with the length of the section 28 divided by the total length, $x \cong 0.8$. Access to each end of the microchannel was provided by a 3 mm hole through the lid piece of the microchannel.

An 8 μmol/L solution of carboxyfluorescein in the 1.8 M Tris/boric buffer was prepared. The analyte to be concentrated was the carboxyfluorescein. Detection of the analyte was performed using a fluorescence microscope and CCD cameras. Simultaneous color and grayscale images were obtained.

To demonstrate gradient focusing using Joule heating, the microchannel was filled with the carboxyfluorescein solution and 1900 V was applied along its length, with the positive voltage $V_2$ applied to the narrow end via electrode 22, and the wide end held at ground at electrode 24.

After 6 min., the carboxyfluorescein was highly concentrated at the junction between sections 26 and 28 of the microchannel 20. The concentration factor achieved by using this example was typically about 100-fold per minute.

Figure 5:
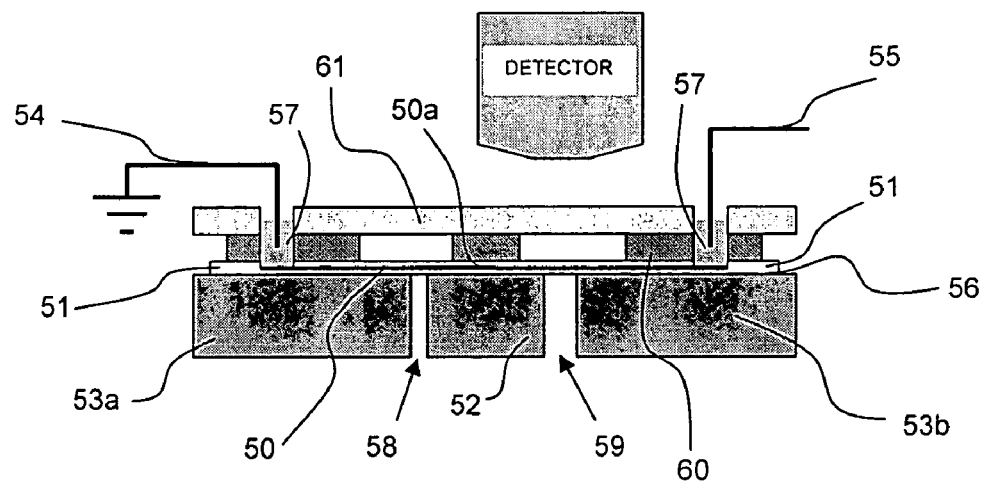
FIG. 5 is a schematic drawing of a fluidic device according to further embodiment of the present invention.

Referring now to FIG. 5, in order to have better control of the temperature gradient, experiments were done using three temperature zones, two cold zones provided by cooling copper blocks 53a, 53b covering much of the ends of the microchannel 50, and one hot zone provided by heated copper block 52. The microchannel 50 was made out of thin (125 μm) sheets of poly(carbonate) substrate 51, which were pressed onto the copper blocks 52, 53a, 53b. Thermal contact between the poly(carbonate) and the copper blocks was insured using a thermally conductive adhesive 56. The copper blocks 52, 53a, 53b were arranged so that there was a 1 mm gap 58 between the heated copper block 52 and the cooling copper block 53a and a 2 mm gap 59 between heated copper block 52 and the cooling copper block 53b.

Microchannel 50 also includes electrodes 55, 54, buffer reservoirs 57, and a narrow hot zone 50a near the middle of the microchannel 50. The heated copper block 52 was heated using a small high-power resistor embedded into the copper and its temperature was regulated using a PID temperature controller (Omega Engineering Inc, Stamford, Conn.). To regulate the temperature of the cold zones, ¼ inch diameter holes were drilled through the cooling copper blocks 53a, 53b and cold water from a thermostatted bath (Neslab, Portsmouth, N.H.) was passed through them.

Thin polycarbonate microchannel chips, i.e. substrate 51 was attached to the copper blocks 52, 53a, 53b using thermally conductive adhesive 56 in the form of transfer tape (3M). The substrate 51 was pressed against the copper blocks 52, 53a, 53b from above with 3 mm thick PDMS (Sylgard 184, Dow Corning, Midland, Mich.) gaskets 60 and a 2 mm thick acrylic (Acrylite OP-4, Cyro Industries, Mt. Arlington, N.J.)) top plate 61, which was secured to the outer copper clocks using nylon screws (not shown).

During temperature gradient focusing, a voltage potential is applied to electrode 55 and electrode 54 is set to ground to allow microchannel 50 to provide focusing and separation of different types of analytes: small dye molecules, amino acids, proteins, DNA, colloidal particles, and cells.

The microchannel 50 may be formed by imprinting with a micro machined silicon template and then sealed with a similar material according to the method disclosed in Ross, D.; Gaitan, M.; Locascio, L. E., *Analytical Chemistry* 2001, 73, 4117–23, herein incorporated by reference.

The copper block arrangement was also used to determine the degree of focusing that could ultimately be reached with temperature gradient focusing. Beginning with a 8 nM solution of Oregon Green 488 carboxylic acid in 1.8 M Tris/boric, 100 min of focusing resulted in a focused plug of Oregon Green 488 carboxylic acid with a peak concentration over 80 µM—a greater than 10000-fold increase in concentration.

It will become readily apparent to one of ordinary skill in the art that the present method provides for use in numerous applications. For example, temperature gradient focusing could be used as a preconcentration step before an analysis or separation or as a simultaneous concentration and separation technique.

In addition, temperature gradient focusing may be used with any charged species in solution and not just small molecules. For example, the analytes may include larger molecules such as proteins and DNA, or even particles and cells. Further, the present method can be used with particles to create packed beds of particles or cells for use in other analysis steps. In addition, the present method can be adapted for use to sort particles or cells by electrophoretic mobility.

In one separation mode, the bulk velocity could be ramped over time to scan focused sample peaks past a fixed detector, e.g. the detector shown in FIG. 5. This would produce results similar to capillary electrophoresis but the widths of the sample peaks would be determined by the applied gradients and the peak heights would be determined by how long a given peak was in the focusing "window". If the ramp speed were halved, the peak heights would all be doubled, so that the ramp rate could be chosen dependent on the concentration limit of detection necessary. Alternatively, the focusing window could remain fixed and a scanning or imaging detector could be used to locate the separate peaks.

In a further embodiment, the method may be adapted for a system where temperature dependence is due to something other than the ionic strength. An example is a system having $f(T)$ constant but $f_{EP}(T)$ not constant, or variable. One way to accomplish this would be to use a buffer with a temperature dependent pH. In such a system, this embodiment of the present invention is similar to isoelectric focusing schemes. However, the present environment differs from isoelectric focusing in that, in the present system, an opposing buffer flow is applied so that analytes are focused at a pH other than their isoelectric points.

When using any of the embodiments of the present method, operating parameters which include voltage, bulk flow rate, and temperature of the different zones may be held constant with time or varied with time to affect the position and width of focused sample peaks. Varying of parameters may be accomplished using any of a number of methods which include the methods previously described above in which the focused sample peaks are scanned past a fixed detector.

Advantageously, in order to achieve the fastest accumulation of analyte in the focused peak, the highest possible voltage should be used. However, a higher applied voltage requires a faster bulk flow which results in greater dispersion, i.e., wider focused peaks, which is disadvantageous for separation and for achieving preconcentration of a sample to a high concentration in a very narrow peak. Therefore, a high voltage and fast bulk flow could be used for the initial accumulation of analyte into a relatively broad peak, and the voltage flow and flow rate could be reduced to the point at which the peak is narrowest. Further, temperature gradients could be turned on and off to first concentrate the sample and then release the focused peak and allow it to flow on down the channel. Further, the temperature gradient can be adjusted to be linear or nonlinear, and the temperature gradient may be monotonic or non-monotonic. Thus, operating parameters may be adjusted to achieve the desired results.

While the previously disclosed embodiments are directed to a microchannel or microfluid device, the present method may be adapted for incorporation for use with substantially larger channels which may include millimeter and centimeter if not larger in dimension which should now be apparent to one of ordinary skill in the art. Because temperature gradient focusing uses low conductivity buffers, one can adapt the present method for use in much larger scale geometries than the micron-sized channels and capillaries described in detail herein.

Figure 6:
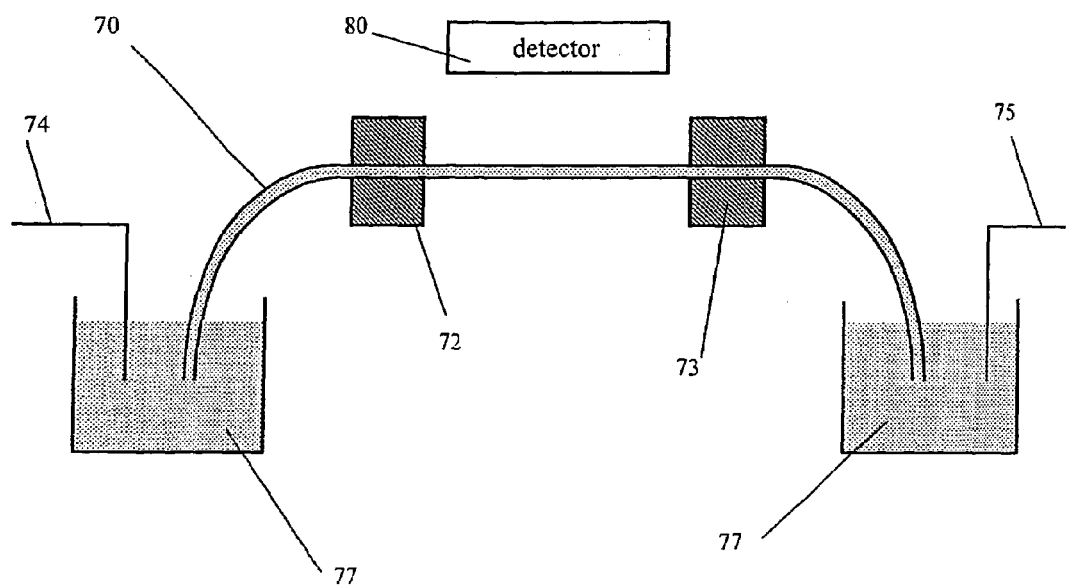
FIG. 6 is a schematic drawing of a capillary fluidic device according to an alternate embodiment of the present invention.

Further, the previously described method can be adapted for use in modified capillary fluidic systems known to one of ordinary skill in the art. FIG. 6 depicts a capillary fluidic system having a capillary tube 70 spanning between two buffer reservoirs 77. Two temperature blocks, denoted as heated block 72 and cooling block 73 are located along the length of the capillary tube 70 to provide a desired temperature gradient in the capillary tube 70. Alternatively, temperature blocks being both cooling, both heated, both at ambient temperature, or any combination, thereof, may be substituted to provide the desired temperature gradient.

The buffer reservoirs 77 contain a buffer with temperature dependent ionic strength. Electrodes 74, 75 are connected at one end to a power supply and on the other end, are in contact with the buffer solution in the buffer reservoirs 77. The power supply applies a driving voltage through the capillary tube 70. A source of bulk flow is driven either by electro-osmosis with the applied driving voltage, by a pressure gradient applied, e.g. by a pump, or a combination of the two. Detector 80 is used to detect analytes present in the buffer solution.

One of ordinary skill in the art now will readily appreciate that the present temperature gradient focusing differs from prior art methods such as sample stacking and isotachophoresis. In both cases, samples are focused or concentrated as a result of gradients in their electrophoretic velocities. In sample stacking and isotachophoresis, the velocity gradients are generated at the interfaces between buffers of different composition, and the point at which the concentration or focusing occurs is not stationary, but moves along with the electroosmotic flow in the channel or capillary. In contrast to both sample stacking and isotachophoresis, the velocity gradients that produce analyte focusing in the present temperature gradient focusing result from applied temperature gradients.

Further, one skilled in the art will recognized that the present temperature gradient focusing differs from isoelectric focusing techniques such as those disclosed in U.S. Pat. Nos. 3,664,939 and 5,759,370. Unlike isoelectric focusing techniques in which the pH gradient is established by using a buffer system that has a temperature dependent pH, the present temperature gradient focusing utilizes a buffer that has a temperature dependent ionic strength. When a temperature gradient and a voltage are applied to a microchannel, the ionic strength gradient of the buffer gives rise to a velocity gradient, which is used for focusing. As a result, an analyte present in the buffer is focused at a point where the analyte's total velocity, i.e., the sum of the electrophoretic velocity and the bulk velocity of the buffer is zero. Therefore, in the present temperature gradient focusing, the pH and the isoelectric point of the analyte are not critical.

It will now be apparent to one of ordinary skill in the art that the present microfluidic device and temperature gradient focusing method provide numerous advantages over prior devices and methods. The present device and method are simpler to implement as no imbedded electrodes or salt bridges are necessary. In addition, like isoelectric focusing, temperature gradient focusing can be used to both concentrate and separate analytes, but without the disadvantages associated with isoelectric focusing.

A further advantage of the present invention is provided in that only a single, continuous buffer system is required. Solid phase extraction and related preconcentration methods of the prior art require multiple buffers where one buffer is used to carry the analyte to the preconcentrator and a second buffer is used to release the analyte from the preconcentrator. Further examples of multiple buffer systems include sample stacking, field amplified injection, iosotachophoresis, and sweeping.

Further, the present temperature gradient focusing provides enhanced concentration when compared with the prior art of other single preconcentration methods.

Although the invention has been described above in relation to preferred embodiments thereof, it will be understood by those skilled in the art that variations and modifications can be effected in these preferred embodiments without departing from the scope and spirit of the invention.

What is claimed is:

1. A method for directing ionic analytes contained in an ionic buffer solution, said ionic buffer solution having a temperature dependent property selected from the group consisting of ionic strength and pH, said method comprising the steps of:
    applying an electric field to an ionic buffer solution containing at least one species of ionic analyte to cause the analyte ions to have electrophoretic motion;
    establishing, in said buffer solution, a temperature gradient having a significant component substantially aligned with the electrophoretic motion of the analyte ions, which produces a gradient in the ionic strength or pH of said buffer solution, thereby generating a gradient of the electrophoretic velocity of the analytes; and
    producing a bulk flow of said buffer solution to have a significant component substantially aligned in the direction opposite the direction of the electrophoretic motion of one or more of the analytes so that at least one of said one or more analytes will accumulate or be focused at at least one point along said temperature gradient, the pH at said at least one point being unequal to the isoelectric point of said at least one of said one or more analytes that are focused at said at least one point.

2. The method of claim 1, wherein said temperature dependent property is ionic strength and said temperature gradient establishes a gradient in the ionic strength of said ionic buffer solution.

3. The method of claim 2, wherein said temperature gradient is applied so as to produce an electrophoretic velocity gradient which concentrates analytes present in the ionic buffer solution.

4. The method of claim 2, wherein said temperature gradient is applied so as to produce gradients in the electrophoretic velocities of the analytes present in the ionic buffer solution thereby causing different analytes to focus at different points within the ionic buffer solution so as to separate the different analytes.

5. The method of claim 2, wherein the analyte is selected from the group consisting of small ions, amino acids, DNA, particles, cells and proteins.

6. The method of claim 2, wherein the bulk flow is generated by electroosmosis.

7. The method of claim 2, wherein the bulk flow is generated by pressure gradients.

8. The method of claim 2, wherein the bulk flow is generated by a combination of electroosmosis and pressure gradients.

9. The method of claim 2, wherein at least one operational parameter selected from the group consisting of temperature, electric field and bulk flow rate is varied over time to affect the position and width of focused sample peaks.

10. The method of claim 2, wherein operational parameters consisting of temperature, electric field, and bulk flow rate are held constant.

11. The method of claim 2, wherein the temperature gradient is one of linear and non-linear.

12. The method of claim 2, wherein the temperature gradient is one of monotonic and non-monotonic.

13. The method of claim 2, wherein the step of establishing a temperature gradient comprises applying an electric current to the ionic buffer solution to produce the temperature gradient by Joule heating.

14. The method of claim 2, wherein the ionic buffer solution is supplied as a continuous single buffer flow.

15. The method of claim 2, wherein the ionic buffer solution and analytes are contained within a microchannel.

16. The method of claim 15, wherein the step of establishing a temperature gradient comprises supplying thermal energy to the microchannel via a heated block.

17. The method of claim 15, wherein the step of applying a temperature gradient comprises cooling a portion of the microchannel using the ambient temperature as a maximum temperature.

18. The method of claim 15, wherein the step of applying a temperature gradient comprises supplying thermal energy to the microchannel via a heated block and removing thermal energy from the microchannel via a cooled block.

19. The method of claim 2, wherein the ionic buffer solution and analytes are contained within a capillary tube.

20. The method of claim 19, wherein the step of establishing a temperature gradient comprises supplying thermal energy to the capillary tube via a heated block.

21. The method of claim 19, wherein establishing a temperature gradient comprises cooling a portion of the capillary tube using ambient temperature as a maximum temperature.

22. The method of claim 19, wherein the step of establishing a temperature gradient comprises supplying thermal energy to the capillary tube via a heated block and removing thermal energy from the capillary tube via a cooled block.

23. The method of claim 1, wherein said temperature dependent property is pH and said temperature gradient establishes a gradient in the pH of said ionic buffer solution, and whereby analytes are focused at a pH other than the isoelectric points of the respective analytes.

24. The method of claim 1, wherein said temperature gradient establishes gradients in both the ionic strength and pH of the ionic buffer solution, and whereby analytes are focused at a pH other than the isoelectric points of the respective analytes.

25. A fluidic device, comprising:
    a fluid conduit;
    an ionic buffer solution with a temperature dependent property selected from the group consisting of ionic strength and pH disposed in said fluid conduit;
    an electric voltage source for providing an electric field within said fluid conduit, thereby causing one or more ionic analytes to have electrophoretic motion;

at least one heat source or heat sink, thermally coupled to said fluid conduit, for providing a temperature gradient having a significant component substantially aligned with the electrophoretic motion of one or more ionic analytes so as to form an electrophoretic velocity gradient within said fluid conduit; and a source of bulk fluid flow for providing flow of said ionic buffer solution in said fluid conduit, in a direction opposite to the electrophoretic motion of at least one of said one or more ionic analytes;

whereby said at least one of said one or more ionic analytes will accumulate or be focused at at least one point along said temperature gradient, the pH at said at least one point being unequal to the isoelectric point of said at least one of said one or more analytes that are focused at said at least one point.

26. The fluid device of claim 25, wherein said temperature dependent property is ionic strength and said temperature gradient establishes a gradient in the ionic strength of said ionic buffer solution.

27. The fluidic device of claim 26, wherein said fluid conduit comprises a microchannel formed in a substrate, having a geometry with at least one spatial dimension on the order of micrometers, and where a temperature gradient is applied to said substrate.

28. The fluidic device of claim 26, wherein said fluid conduit comprises a channel formed in a substrate and having a geometry with at least one spatial dimension on the order of at least one millimeter, and where a temperature gradient is applied to said substrate.

29. The fluidic device of claim 26, wherein said fluid conduit comprises a channel formed in a substrate and having a geometry with at least one spatial dimension on the order of at least one centimeter, and where a temperature gradient is applied to said substrate.

30. The fluidic device of claim 26, wherein said at least one heat source comprises a power supply for applying an electrical current to said fluid conduit to thereby generate the temperature gradient in said ionic buffer solution by Joule heating.

31. The fluidic device of claim 26, wherein said at least one heat source comprises a heated block for providing thermal energy to said fluid conduit.

32. The fluidic device of claim 31, wherein said at least one heat sink further comprises a cooling block spaced from said heated block and thermally coupled to said fluid conduit for removing thermal energy from said fluid conduit.

33. The fluidic device of claim 31, further comprising a thermally conductive adhesive disposed between said heated block and said fluid conduit.

34. The fluidic device of claim 26, wherein said at least one heat sink comprises a cooling block for removing thermal energy from said fluid conduit.

35. The fluidic device of claim 34, wherein said heat source comprises a power supply for applying an electrical current to said fluid conduit to thereby generate the temperature gradient in said fluid conduit.

36. The fluidic device of claim 26, wherein said fluid conduit comprises a capillary tube.

37. The fluid device of claim 25, wherein said temperature dependent property is pH and said temperature gradient establishes a gradient in the pH of said ionic buffer solution, and whereby analytes are focused at a pH other than the isoelectric points of the respective analytes.

* * * * *